(12) United States Patent
Pallecchi et al.

(10) Patent No.: US 11,382,948 B2
(45) Date of Patent: Jul. 12, 2022

(54) ASSOCIATION OF N-ACETYLCYSTEINE AND COLISTIN FOR USE IN BACTERIAL INFECTIONS

(71) Applicant: Zambon S.P.A., Bresso (IT)

(72) Inventors: Lucia Pallecchi, Colle di val D'Elsa (IT); Francesco Sergio, Bresso (IT); Gian Maria Rossolini, Siena (IT)

(73) Assignee: Zaambon S.P.A., Bresso (IT)

( * ) Notice: Subject to any disclaimer, the term of this patent is extended or adjusted under 35 U.S.C. 154(b) by 116 days.

(21) Appl. No.: 16/487,227

(22) PCT Filed: Feb. 26, 2018

(86) PCT No.: PCT/EP2018/054611
§ 371 (c)(1),
(2) Date: Aug. 20, 2019

(87) PCT Pub. No.: WO2018/154091
PCT Pub. Date: Aug. 30, 2018

(65) Prior Publication Data
US 2021/0128678 A1 May 6, 2021

(30) Foreign Application Priority Data

Feb. 27, 2017 (EP) .................................... 17158241

(51) Int. Cl.
| | | |
|---|---|---|
| *A61K 38/12* | (2006.01) | |
| *A61K 31/198* | (2006.01) | |
| *A61K 31/164* | (2006.01) | |
| *A61P 31/04* | (2006.01) | |

(52) U.S. Cl.
CPC ............ *A61K 38/12* (2013.01); *A61K 31/198* (2013.01); *A61P 31/04* (2018.01)

(58) Field of Classification Search
CPC .............. A61K 31/164; A61K 2300/00; A61K 31/198; A61K 38/12; A61P 31/04
See application file for complete search history.

(56) References Cited

FOREIGN PATENT DOCUMENTS

| WO | 1998020836 A2 | 5/1998 |
|---|---|---|
| WO | 2004022048 A1 | 3/2004 |
| WO | 2012080700 A1 | 6/2012 |

OTHER PUBLICATIONS

Blasi et al, "The effect of N-acetylcysteine on biofilms: Implications for the treatment for respiratory tract infections," Respiratory Medicine, 2016, 117: 190-197 (Year: 2016).*
Qureshi et al, "Colistin-Resistant Acinetobacter baumannii: Beyong Carbapenem Resistance," Clinical Infectious Disease, 2015, 60: 1295-1303. (Year: 2015).*
Hogardt et al, "Pitfalls of polymyxin antimicrobial susceptibility testing of Pseudomonas aeruginosa isolated from cystic fibrosis patients," Journal of Antimicrobial Chemotherapy, 2004, 54: 1057-1061. (Year: 2004).*
Sergio et al., "Synergistic activity of N-acetylcysteine and colistin against Stenotrophomonas maltophilia," European Respiratory Journal, Dec. 6, 2017, 50(Suppl 61), pp. 1-5 as enclosed. (Year: 2017).*
Alfredsson H., et al., "N-acetylcysteine and 2-mercaptoethane sulphonate inhibit anti-pseudomonas activity of antibiotics in vitro", Eur J Respir Dis (1987) 70, 213-217.
Drago L., et al., "Activity of N-acetyl-L-cysteine against biofilm of Staphylococcus aureus and Pseudomonas aeruginosa on orthopedic prosthetic materials", Int j. Artif Organs 2013; 36(1): 36-46.
Jaruratanasirikul S., et al., "Population pharmacokinetics and pharmacodynamics modeling to optimize dosage regimens of sulbactam in critically ill patients with severe sepsis caused by Acinetobacter baumannii," Antimicrobial Agents and Chemotherapy, Dec. 1, 2016, vol. 60, No. 12, pp. 7236-7244.
Search Report and Written Opinion of PCT/EP2018/054611 dated Mar. 26, 2018.

* cited by examiner

*Primary Examiner* — Julie Ha
(74) *Attorney, Agent, or Firm* — Silvia Salvadori, P.C.; Silvia Salvadori (57) ABSTRACT

A synergistic pharmacological association of N-acetylcysteine (NAC) and colistin for use in the treatment of a bacterial infection caused by one or more pathogens selected from *S. maltophilia* and *A. baumannii* strains, in particular a bacterial infection associated with a respiratory tract disease, such as a chronic respiratory tract disease comprising cystic fibrosis (CF), bronchiectasis non CF and chronic obstructive pulmonary disease (COPD) is described.

13 Claims, 4 Drawing Sheets

ASSOCIATION OF N-ACETYLCYSTEINE AND COLISTIN FOR USE IN BACTERIAL INFECTIONS

This application is a U.S. national stage of PCT/EP2018/054611 filed on 26 Feb. 2018, which claims priority to and the benefit of European Patent Application No. 17158241.4, filed on 27 Feb. 2017, the contents of which are incorporated herein by reference in their entireties.

FIELD OF THE INVENTION

The present invention relates to a synergistic pharmacological association of N-acetylcysteine (hereinafter NAC) and colistin for use in the treatment of bacterial infections caused by one or more pathogens selected from *Stenotrophomonas maltophilia* (*S. maltophilia*) and *Acinetobacter baumannii* (*A. baumannii*) strains. In particular, the present invention relates to a synergistic pharmacological association of NAC and colistin for use in the treatment of a disease associated with bacterial infections caused by one or more pathogens selected from *S. maltophilia* and *A. baumannii* strains, particularly for use in the treatment of a respiratory tract disease.

BACKGROUND OF THE INVENTION

Colistin, also termed polymixin E, a polymixin antibiotic produced by certain strains of *Bacillus polymixa*, consists of a cationic cyclic heptapeptide with a tripeptide side chain acylated at the N terminus by a fatty acid through an α-amide linkage (Reviews of Anti-Infective Agents CID 2005; 40: 1033-41).

Two different forms of colistin are available for clinical use: colistin sulfate which is administered orally for bowel decontamination and topically as a powder for the treatment of bacterial skin infections, and colistimethate sodium (CMS) (also called colistin methanesulfate, pentasodium colistimethanesulfate, and colistin sulfonyl methate) for parenteral (intravenous, intramuscular, aerosolized and intrathecal/intraventricular) therapy.

Colistin can be therefore administered as a prodrug in form of colistimethate sodium, which is readily idrolized to form sulfomethylated derivatives, as well as colistin sulfate, the active form of the drug.

Colistin has recently gained a crucial role for the treatment of various types of infections (e.g. pneumonia, bacteremia, urinary tract infections) caused by Gram-negative pathogens expressing a multidrug resistance phenotype (e.g. non-fermenting Gram-negative pathogens, and carbapenem-resistant enterobacteria).

In patients affected by cystic fibrosis or other chronic respiratory diseases, it is commonly used to treat infections caused by *Pseudomonas aeruginosa* (*P. aeruginosa*) or other multidrug resistant non-fermenting Gram-negative pathogens (e.g. *Acinetobacter baumannii, Stenotrophomonas maltophilia*).

Colistin represents a last-resort agent for the treatment of infections caused by multidrug resistant *A. baumannii*. In this perspective, great concerns arise from the rising trend of resistance to colistin in *A. baumannii*, which often results in pan-drug resistance phenotypes (PDR), with no available treatment option left.

Treatment of *S. maltophilia* infections is complicated by intrinsic multidrug resistance. In case the first line treatment based on trimethoprim-sulphamethoxazole is not suitable (for patient intolerance or acquired resistance), colistin is among the second line options, with the advantage of being also administrable by nebulization. However, increasing colistin resistance rates in *S. maltophilia* have been documented, representing a matter of great concern.

Colistimethate sodium is a combination of the negatively charged molecular ion colistin sulphomethate with positive sodium ions.

Colistimethate sodium can be produced by a sulfomethylation reaction of colistin with formaldehyde followed by sodium bisulfite, which leads to the addition of a sulfomethyl group to the primary amines of colistin (Antimicrob. Agents Chemother. April 2003 vol. 47 no. 4 1364-1370).

Colistimethate sodium is commercially available under various brand names by different manufacturers throughout the world, for example as Promixin™ (Profile Pharma Limited).

According to the present invention the term "colistin" includes colistin and its pharmaceutically acceptable salts and/or prodrugs such as colistin sulfate, colistimethate sodium, colistin methane sulphate and colimycin or colomycin, all intended to refer to the bactericidal cyclopeptide antibiotic colystin or precursors thereof such as the prodrug colimycin which is converted to the active drug colistin. In a particular aspect, for in vitro susceptibility testing in the experimental part of the present invention the term "colistin" refers to colistin sulfate (in accordance with the international guidelines for antimicrobial susceptibility testing provided by the Clinical and Laboratory Standards Institute—CLSI and the European Committee on Antimicrobial Susceptibility Testing—EUCAST).

NAC is the acetylated precursor of both the amino acid L-cysteine and reduced glutathione (GSH). Historically it has been used as a mucolytic agent with antioxidant and anti-inflammatory properties, in patients who have viscid or thickened airway mucus for a range of chronic respiratory illnesses, including chronic bronchitis, emphysema, COPD and exacerbations, cystic fibrosis, bronchiectasis, as an antidote due to acetaminophen overdose and as a potential treatment of diseases characterized by free radical, oxidant damage.

NAC can be typically considered a non-antibiotic drug, to which antibacterial and antibiofilm properties have been associated in some cases. For example, in 1977, Parry and Neu found that NAC had the characteristics to inhibit the growth of both gram-positive and gram-negative bacteria, including *Staphylococcus aureus, P. aeruginosa, Klebsiella pneumoniae* and *Enterobacter cloacae* (Journal of Clinical Microbiology, January 1977, p. 58-61).

In the literature, controversial results have been reported regarding the interference of antibiotics and mucolytic agents such as NAC. In 1981, Roberts and Cole found that 2%-5% of NAC exhibited antimicrobial activity against *P. aeruginosa* and that the effect of the carbenicillin on *P. aeruginosa* was augmented by low concentrations of NAC (Journal of Infection Volume 3, Issue 4, December 1981, Pages 353-359). In 2016, the result of a study carried out by Landini et al. on the effect of high NAC concentrations on antibiotic activity against a collection of respiratory pathogens, demonstrated that high NAC concentrations do not interfere with the activity of the most commonly used antibiotics, whereas NAC compromised the activity of carbapenems (Antimicrob. Agents Chemother. December 2016 vol. 60 no. 12 7513-7517).

NAC is commercially available under various brand names by different manufacturers throughout the world, for example as Fluimucil™ (Zambon Spa). *S. maltophilia* infections are commonly associated with respiratory tract diseases, in particular chronic respiratory tract diseases; for example, *S. maltophilia* infections can trigger pulmonary exacerbations of chronic obstructive lung disease (COPD), Cystic Fibrosis (CF) and bronchiectasis non CF.

*S. maltophilia* infections occur principally, but not exclusively, in debilitated and immunosuppressed individuals.

*S. maltophilia* are characterized by a multidrug resistance phenotype and the ability to form biofilms. In virtue of these features, they are responsible for chronic lung colonization in individuals with weakened immune systems or chronic lung disease, particularly CF and bronchiectasis non CF, which may last several months or years and are difficult or impossible to be eradicated by current antibiotic treatment strategies.

As *S. maltophilia*, *A. baumannii* is an important and difficult-to-treat pathogen, which can infect the respiratory tract of patients affected by respiratory tract diseases, including chronic respiratory tract diseases. For example, the presence of *A. baumannii* infections in patients with pneumonia, in particular, in ventilator-associated pneumonia (VAP), represents one of the most dreadful complications that occur in the critical care setting.

*A. baumannii* has been also identified in the CF population and in the population with bronchiectasis non CF.

The association of *A. baumannii* infections with bacteremia, wound infections, urinary tract infections and meningitis has been also described. It can be noted that there has been a dramatic increase in the number of *A. baumannii* strains with resistance to multiple antibiotic classes and the multidrug-resistant nature of this pathogen represents a challenge in the treatment and control of nosocomial infections, with relatively limited treatment options. For example, nosocomial pneumonia due to multidrug resistant gram-negative bacteria comprising *A. baumannii*, is among the most serious complications that occur in the intensive care unit (ICU) setting. Mortality, morbidity and health care costs are substantially increased by this type of infection.

Despite a significant amount of time and energy has been devoted to studying effective treatments for dealing successfully with bacterial infections, especially of the airway and/or lung, caused by a range of pathogens including emerging pathogens such as *S. maltophilia* and *A. baumannii*, there is substantially lack of good therapeutic options and hence there remains a need for better treatments of said bacterial infections, in particular those associated with chronic lung diseases such as, for example, CF, bronchiectasis non CF and COPD.

SUMMARY OF THE INVENTION

Accordingly, the present inventors faced the problem of treating a bacterial infection caused by one or more pathogens selected from *S. maltophilia* and/or *A. baumannii*. After a long set of tests and experimentations, the present inventors have surprisingly found that the association of NAC and colistin has a synergistic antimicrobial effect against a consistent number of *S. maltophilia* and/or *A. baumannii* clinical isolates, even resulting in a bactericidal effect.

The association of NAC and colistin has also been found to have synergistic anti-biofilm activity in in vitro biofilm models of *S. maltophilia* and/or *A. baumannii* The anti-biofilm activity of the association of NAC and colistin against *S. maltophilia* and/or *A. baumannii* biofilms envisages a potential use also for both preventing and eradicating colonization by said pathogens, especially in the hospitalized patients affected by diseases including, for example, chronic bronchitis, emphysema, COPD and exacerbations, CF, bronchiectasis non CF, pneumonia, VAP, bacteremia, wound infections, urinary tract infections and meningitis.

More in detail, the present inventors noticed that with an increase in the use of colistin to treat infections caused by multidrug resistant Gram-negative pathogens, resistance to colistin has been increasingly reported.

Since colistin represents one of the last therapeutic options to fight Gram-negative bacteria, the appearance of colistin-resistant Gram-negative pathogens such as *S. maltophilia* and/or *A. baumannii* is of great concern.

The present inventors, by concentrating their efforts in identifying an effective treatment able to restore susceptibility of said pathogens to the colistin treatment, have unexpectedly found that colistin effectiveness against colistin-resistant Gram-negative pathogens such as, e.g., *A. baumannii* and *S. maltophilia* can be surprisingly restored by administering colistin together with NAC. In particular, the MIC of all colistin resistant strains tested lowered at or below the susceptibility breakpoint in the presence of NAC 8 mg/ml.

DETAILED DESCRIPTION OF THE INVENTION

It is therefore a first aspect of the present invention a synergistic pharmacological association of NAC and colistin for use in inhibiting or suppressing the growth and/or killing a strain of a pathogen selected from *S. maltophilia* and *A. baumannii* strains.

It is another aspect of the present invention a synergistic pharmacological association of NAC and colistin for use in the treatment of a bacterial infection caused by one or more pathogens selected from *S. maltophilia* and *A. baumannii* strains, in particular a bacterial infection associated with a respiratory tract disease, particularly a chronic respiratory tract disease such as e.g., CF, bronchiectasis non CF and COPD.

In a particular aspect, a bacterial infection is caused by a pathogen selected from S. maltophilia and A. baumannii strains, either expressing a colistin susceptible or resistant phenotype; especially, a pathogen selected from S. maltophilia and A. baumannii strains, expressing a colistin resistant phenotype.

A bacterial infection caused by S. maltophilia strain can be detected, for example, in patients suffering from respiratory tract diseases, particularly chronic respiratory tract diseases such as, for example, in patients suffering from COPD, CF or bronchiectasis non CF, especially when these patients have weakened immune systems.

A bacterial infection caused by A. baumannii strain can be detected, for example, in patients suffering from pneumonia, VAP, bacteremia; wound infections, urinary tract infections, CF and bronchiectasis non CF, especially when these patients are hospitalized patients.

In a more particular aspect of the present invention, patients suffering of a bacterial infection caused by a pathogen selected from S. maltophilia and A. baumannii strains as described above are immunocompromised and/or hospitalized patients.

A bacterial infection caused by a pathogen selected from S. maltophilia and A. baumannii strains according to the present invention may be a biofilm-associated infection.

The above aspects are based on the observation that there is a synergistic interaction between NAC and colistin, which provides a significant antibacterial effect.

According to the present invention the terms "synergistic" and "synergistically" as applied to the effect of NAC and colistin used in association (whether simultaneously or sequentially) refer to a greater antibacterial effect obtained when the above-identified bacteria are treated by either NAC or colistin alone. In some embodiments, the effect of NAC and colistin used in association (whether simultaneously or sequentially) is greater than the simple addition of the effects of each agent administered alone, i.e. there is an effect which surpasses expectations based on additive effects.

It is a further aspect of the present invention a synergistic pharmacological association of NAC and colistin for use in the treatment of a bacterial infection caused by one or more pathogens selected from colistin-resistant S. maltophilia and colistin-resistant A. baumannii strains, wherein NAC is able to restore susceptibility of said pathogens to colistin.

It is a further aspect of the present invention a pharmacological association of NAC and colistin for use in the treatment of a bacterial infection caused by one or more pathogens selected from colistin-susceptible S. maltophilia and colistin-susceptible A. baumannii strains, wherein NAC is able to prevent in vivo emergence of colistin resistance, during colistin treatment regimens.

NAC and colistin of the pharmacological association according to the present invention may be administered in either order, separately or concurrently, with overlapping or non-overlapping periods of administration, via the same or different modes of administration.

For example, NAC and colistin can be concurrently administered in a single dosage form or alternatively NAC and colistin can be administered in separate dosage forms in either order, concomitantly or sequentially, with overlapping or non-overlapping periods of administration, via the same of different modes of administration.

The concurrent or separate administration of the pharmacological association of NAC and colistin has the effect of in inhibiting or suppressing the growth and/or killing a strain of a pathogen selected from S. maltophilia and A. baumannii strains, said effect being unexpectedly and surprisingly greater than what is seen when bacteria are contacted by either NAC or colistin alone.

In detail, the present inventors noticed that with an increase in the use of colistin to treat infections caused by multidrug resistant Gram-negative pathogens, resistance to colistin has been increasingly reported.

Since colistin represents one of the last antibiotic resorts to fight Gram-negative bacteria, the appearance of colistin-resistant Gram-negative pathogens is of great concern.

The present inventors strongly perceived the great need of an effective treatment against colistin-resistant Gram-negative pathogens such as, e.g., A. baumannii and S. maltophilia, able to restore susceptibility of said pathogens to the antibiotic treatment, or to prevent in vivo emergence of colistin resistance during colistin treatment regimens.

The present inventors have found that colistin effectiveness against colistin-resistant Gram-negative pathogens such as, e.g., A. baumannii and S. maltophilia can be surprisingly restored by the administration of the association of NAC with colistin.

In particular, colistin susceptibility can be restored by NAC concentrations possibly achievable by topical administration. In particular, the MIC of all colistin resistant strains tested lowered at or below the susceptibility breakpoint in the presence of NAC 8 mg/ml.

The association of NAC and colistin may be administered to the patient in the form of one or more pharmaceutical formulations.

The pharmaceutical formulations of the present invention comprise NAC and/or colistin together with a carrier suitable for pharmaceutical use, consisting of one or more excipients. For example, the pharmaceutical formulations of the invention may comprise both NAC and colistin together with a carrier suitable for pharmaceutical use, consisting of one or more excipients, i.e. pharmaceutical formulations for concurrent administration of both NAC and colistin; or the pharmaceutical formulations of the invention may comprise NAC together with a carrier suitable for pharmaceutical use, consisting of one or more excipients; or the pharmaceutical formulations of the invention may comprise colistin together with a carrier suitable for pharmaceutical use, consisting of one or more excipients, i.e. separate pharmaceutical formulations for sequential or concomitant administration of NAC and colistin.

According to the present invention, the term "excipient" comprises any inert substance added to a pharmaceutical composition to further facilitate administration of an active ingredient.

According to the present invention, the term "carrier" comprises any substance suitable as a vehicle for delivering NAC and/or colistin to a suitable in vivo or in vitro site.

Pharmaceutically acceptable excipients are those compounds well known to a skilled person in the art that can be used to produce formulations comprising NAC and/or colistin that are suitable to be administered to a subject. Acceptable methods for preparing the pharmaceutical formulations according to the invention are well known to a person skilled in the art.

It is a further object of the present invention a method of treating a bacterial infection caused by a pathogen selected from S. maltophilia and A. baumannii strains in a subject in need thereof, which comprises administering an association comprising NAC and colistin, wherein the association has a synergistic antibacterial effect.

It is a further object of the present invention a method of treating a bacterial infection caused by a pathogen selected from S. maltophilia and A. baumannii strains in a subject in need thereof, which comprises concurrently administering an association comprising NAC and colistin, wherein the association has a synergistic antibacterial effect.

It is a further another object of the present invention a method of treating a bacterial infection caused by a pathogen selected from S. maltophilia and A. baumannii strains in a subject in need thereof, which comprises separately administering an association comprising NAC and colistin, wherein the association has a synergistic antibacterial effect.

According to the present invention, the terms "individual" "subject" and "patient" are used interchangeably to refer to a member of mammalian specie, preferably a human, which is afflicted with a particular disease, disorder or condition.

According to the present invention the term "antibacterial" means reducing the harmful effects of bacteria by inhibiting, suppressing the growth and/or killing them. According to the present invention the term "antibacterial agents" includes NAC and colistin.

According to the present invention the term "bactericidal" means having a destructive killing action upon bacteria.

According to the present invention, "bacterial infection" refers to any situation in which the presence of a microbial population(s) is damaging to a host mammal. Thus, an individual is "suffering" from a microbial infection when excessive numbers of a microbial population are present in or on an individual's body, or when the effects of the presence of a microbial population(s) is damaging the cells or other tissue of an individual. In particular, "bacterial infection" refers to an infection caused by a strain of bacteria for which the use of a synergistic pharmacological association of NAC and colistin disclosed herein is appropriate.

According to the present invention, the terms "treat", "treating" and "treatment" refer to a diminution, a decrease, a limitation, or a mitigation of the degree, intensity, extent of a bacterial infection or its related disease conditions and symptoms caused by a strain of S. maltophilia and/or A. baumanii, that is achieved by a reduction, inhibition or suppression of growth, replication, and/or propagation, or death or destruction of said bacteria, on or in the subject.

According to the present invention, the term "pharmacological association" refers to either a fixed combination of NAC and colistin in one unit dosage form, a non-fixed combination or a kit of parts for the combined administration where NAC and colistin, as defined above, may be administered simultaneously, independently at the same time or separately within time intervals that allow the combination partners to show a synergistic effect.

Any suitable route of administration may be used for the compositions of the present invention, including oral, parenteral (subcutaneous, intramuscular or intravenous) and inhalation route.

According to the present invention, the terms "oral" or "orally" refer to the introduction into the body by mouth whereby absorption occurs in one or more of the following areas of the body: the mouth, stomach, small intestine, and the small blood vessels of the oral mucosa.

Non-limiting examples of pharmaceutical formulations according to the present invention for oral administration include, for example, tablets, coated tablets, granulates, pills, capsules, liquids, gels, syrups, suspensions, and the like, for oral ingestion by an individual. Suitable carriers for oral administration are well known in the art.

For parenteral administration, pharmaceutical formulations according to the invention may be formulated for example in aqueous solutions such as in physiologically compatible buffers or physiological salt buffer. Formulations for injection may be presented in unit dosage forms, for example, in ampoules, or in multi-dose containers with, optionally, an added preservative.

For administration by inhalation route, pharmaceutical formulations according to the invention may be formulated in solutions, suspensions and dry powder and delivered by using conventional means, so that optimal quantities of a suitable range of particle sizes are provided to the patient.

The pharmaceutical formulations according to the invention may be preferably administered to the respiratory tract. Thus, the present invention also provides aerosol pharmaceutical formulations comprising NAC and/or colistin.

Pharmaceutical compositions of the present invention may be manufactured in conventional manners, following processes well known in the art.

The amount of NAC and colistin for use according to the present invention may vary depending on the administration route, the selected kind of composition, the individual characteristics of the patient, the duration of the treatment and the nature of concurrent therapies.

For example, the synergistic effective amount of the pharmacological association of NAC and colistin can produce a diminution, a decrease, a limitation, or a mitigation of the degree, intensity, extent of a bacterial infection or its related symptoms caused by a strain of A. baumannii and/or S. maltophilia.

According to one embodiment, the amount of NAC and colistin sufficient to have a synergistic effect on a bacterial infection caused by a strain of A. baumannii and/or S. maltophilia may vary, for example, in view of the physical characteristics of the patient, the severity of the subject's symptoms, the form of the infection, the identity of the bacteria, the formulations and the means used for administering the drug. The specific dose for a given subject is usually set by the judgement of the attending physician.

However, as an example, an effective amount of colistin may be between about 0.075 million units and 12 million units (i.e. between about 6 mg and 960 mg), preferably between about 0.5 million units and 12 million units (i.e. between about 40 mg and 960 mg); the effective amount of NAC may vary between 100 and 5800 mg, preferably between 100 and 4600 mg, to be administered in a single dose or in more repeated doses.

Depending of the means of administration a dose may be administered all at once or slowly over a period of time, such as with an i.v. or by inhalation administration. According to the present invention, the term "dose", "unit dose", "dosage", "effective dose" and related terms refer to physically discrete units that contain a predetermined quantity of active ingredient calculated to produce a desired therapeutic effect. A single dose is thus a predetermined quantity of colistin or NAC that is administered to a patient.

The exact composition, route of administration, and dosage can be chosen by the individual physician in view of the patient's condition. Treatment should be continued for as long as required to receive the benefit of the invention.

A determination of a synergistic interaction between NAC and colistin may be based on the results obtained from the assays described here below.

In vitro antimicrobial synergism between NAC and colistin was determined following EUCAST guidelines. In particular, the total fractional inhibitory concentration ($\Sigma$FIC) was calculated as follows: $\Sigma$FIC equals FIC of agent A plus

Example 1

Activity of NAC in association with colistin against *A. baumannii* Seven colistin resistant *A. baumannii* clinical isolates were included in the study (colistin MIC range 16-256 µg/ml, MIC50=64 µg/ml, MIC90=128 µg/ml). Classic checkerboard assays were used to investigate potential synergism between colistin (range 0.25-256 µg/ml) and NAC (range 0.5-32 mg/ml). Fraction inhibitory concentration indices (FICIs) were calculated, and synergism was defined as FICI values <0.5. Synergy between colistin and NAC was also confirmed by time-kill assays performed with one isolate, using two different concentrations of colistin (2 and 8 µg/ml, representing concentrations achievable in serum and epithelial lining fluid—ELF, respectively) and NAC (1.6 and 8 mg/ml, likely achievable in ELF by topical administration).

Figure 1:
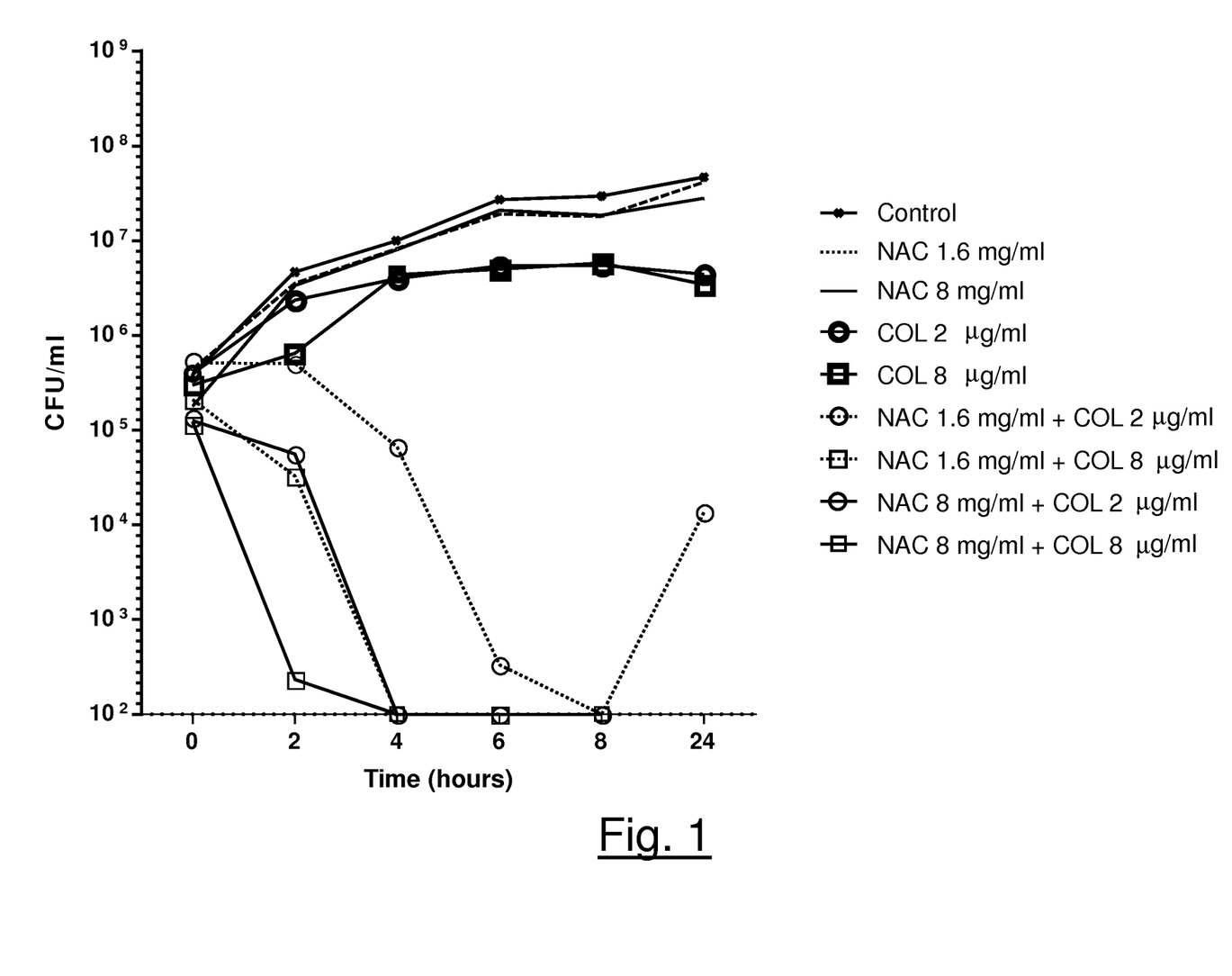
FIG. 1. Time kill curves. NAC alone (1.6 and 8 mg/ml), colistin alone (2 and 8 µg/ml and combination NAC+colistin (1.6 mg/ml+2 µg/ml, 1.6 mg/ml+8 µg/ml, 8 mg/ml+2 µg/ml, 8 mg/ml+8 µg/ml). Symbols: -♦- : Control; ---- (dotted line): NAC 1.6 mg/ml; ━━: NAC 8 mg/ml; -O- Colistin 2 mg/ml; -□- Colistin 8 µg/ml; ----○---- (dotted line) NAC 1.6 mg/ml+Colistin 2 µg/ml; ----□---- (dotted line): NAC 1.6 mg/ml+Colistin 8 µg/ml; ─○─ : NAC 8 mg/ml+Colistin 2 µg/ml; ─□─ : NAC 8 mg/ml+Colistin 8 µg/ml.

The MIC of NAC was 32 mg/ml for two isolates, and >32 mg/ml for the remaining ones. Synergism between colistin and NAC was observed in checkerboard assays with all tested isolates. In particular, a restoration of colistin susceptibility (i.e. MIC ≤2 µg/ml) was observed with 100% and 52% of tested strains in the presence of NAC 4 mg/ml and NAC 2 mg/ml, respectively. Time-kill curves confirmed the synergy observed by checkerboard assays, demonstrating a bactericidal effect of colistin/NAC combinations at sub-MIC concentrations (FIG. 1 shows the curves obtained with isolate N50, with NAC MIC=>32 mg/ml and Colistin MIC=16 µg/ml).

In order to further investigate the synergism of colistin/NAC combinations against colistin-resistant *A. baumannii* strains, time-kill assays were also performed according to CLSI guidelines with two selected strains (i.e. Z165 and Z167, $Col^R$). Two colistin concentrations (i.e. 2 and 8 µg/ml), and three NAC concentrations (i.e. 1.6, 3.2 and 8 mg/ml) were tested alone and in combination with colistin, with determination of viable cells performed after 0, 2, 4, 6, 8, 24 and 48 hours of exposure (detection limit 25 CFU/ml). Data were obtained in two independent experiments, with two replicates per condition per experiment and show a dose-dependent potentiation of colistin activity by NAC. In particular, a complete eradication of the starting inocula was achieved with combinations including NAC 8 mg/ml (i.e. absence of regrowth after 48 hours of incubation).

A biofilm eradication test on the two isolates was also carried out as follows: biofilms were grown in the NUNC TSP lid system (MBEC assay), for seven days in daily refreshed CAMHB (static conditions). Preformed biofilms were then exposed to two colistin concentrations (i.e. 2 and 8 µg/ml), and three NAC concentrations (i.e. 1.6, 3.2 and 8 mg/ml), alone and in combination, for 24 hours. After exposure, biofilms were disrupted by sonication and mean viable cell count per peg (log CFU/peg) was determined (detection limit 1.3 log CFU/peg). Data were obtained in at least two independent experiments, with at least six replicates per condition per experiment.

Results showed a remarkable antibiofilm synergistic activity of combinations including colistin 8 µg/ml (i.e. representing 0.25× and 0.06×MIC for Z165 and Z167, respectively), with a marked reduction of viable biofilm cells also observed in the presence of the lower NAC concentration tested (i.e. 1.6 mg/ml).

Example 2

Activity of NAC in Association with Colistin Against *S. maltophilia*

Figure 2A:
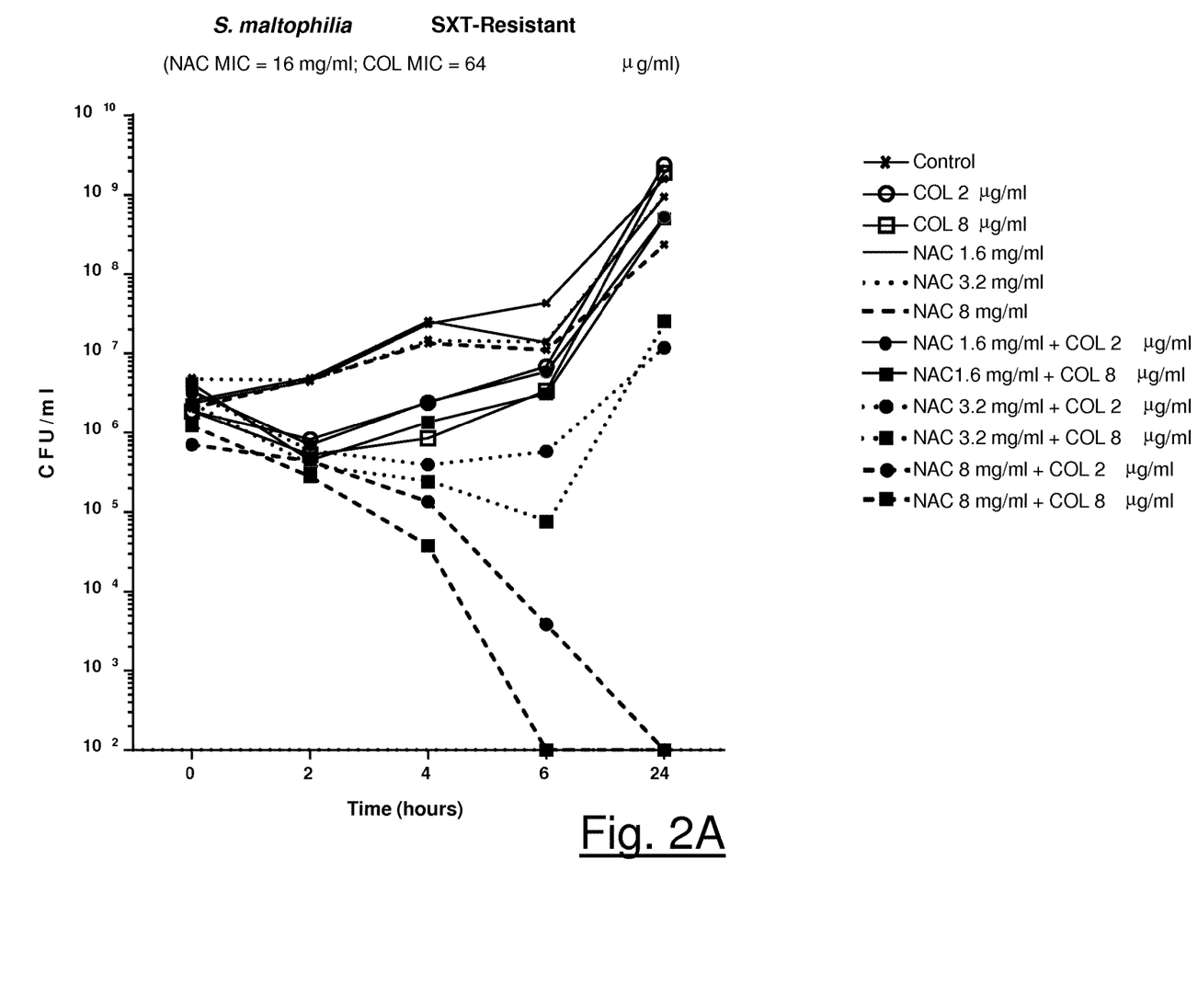
FIG. 2. Time kill curves of *S. maltophilia* isolates with sub MIC concentrations of N-acetylcysteine (NAC 1.6, 3.2 and 8 mg/ml) and colistin (COL 2, 8 µg/ml) alone and in combination. A) STX: trimethoprim-sulphametoxazole resistant *S. maltophilia* strain; B) *S. maltophilia* CF: strain from a Cistic Fibrosis patient. Symbols: -X- : Control; ─○─ Colistin 2 µg/ml; ─□─ Colistin 8 µg/ml; ━━: NAC 1.6 mg/ml; ---- (dotted line) NAC 3.2 mg/ml; - - - (dashed line) NAC 8 mg/ml; -●- : NAC 1.6 mg/ml+Colistin 2 µg/ml; -■- : NAC 1.6 mg/ml+Colistin 8 µg/ml; ----●---- (dotted line) NAC 3.2 mg/ml+Colistin 2 µg/ml; ----■---- (dotted line) NAC 3.2 mg/ml+Colistin 8 µg/ml; - - ●- - (dashed line): NAC 8 mg/ml+Colistin 2 µg/ml; - -■- - (dashed line): NAC 8 mg/ml+Colistin 8 mg/ml.
Figure 2B:
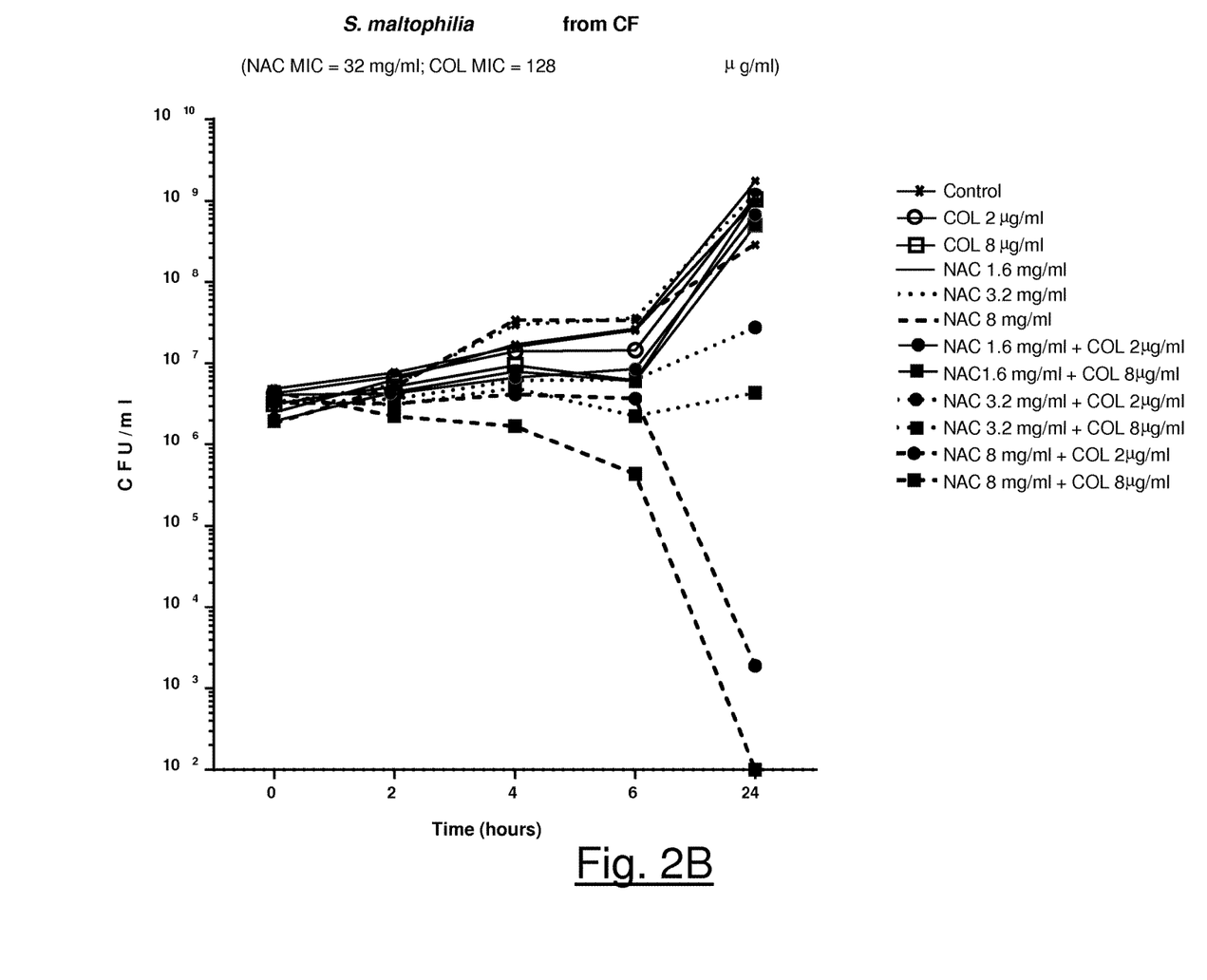

Twenty *S. maltophilia* clinical isolates were tested, including also four isolates from patients affected by cystic fibrosis (CF). Two isolates showed resistance to trimethoprim-sulphamethoxazole. Synergism between colistin (range 0.25-256 µg/ml) and NAC (range 0.5-32 mg/ml) was investigated by classic checkerboard assays. Fraction inhibitory concentration indices (FICIs) were calculated, and synergism was defined as FICI values <0.5. Time-kill assays were performed with two clinical isolates (including one strain resistant to trimethoprim-sulphamethoxazole, and one from CF). For this purpose, two different concentrations of colistin (2 and 8 µg/ml, representing concentrations achievable in serum and epithelial lining fluid—ELF, respectively) and NAC (1.6 and 8 mg/ml, likely achievable in ELF by topical administration) were tested alone and in combination. Colistin MICs ranged from 0.5 µg/ml to 128 µg/ml (MIC50, 16 µg/ml; MIC90, 64 µg/ml). The MIC of NAC was 16 mg/ml for nine isolates, >32 mg/ml for one isolate, and 32 mg/ml for the remaining ones. Synergism between colistin and NAC was observed in checkerboard assays with all tested isolates. In particular, NAC 8 mg/ml and 2 mg/ml lowered colistin MIC to ≤2 µg/ml (the susceptibility breakpoint for *A. baumannii* and *P. aeruginosa*) for 100% and 47% of isolates with colistin MIC>2 µg/ml (n=17), respectively. Time-kill curves confirmed the synergy observed by checkerboard assays, demonstrating a bactericidal effect of colistin/NAC combinations at sub-MIC concentrations (FIGS. 2 A and B).

The antibiofilm activity of colistin/NAC combinations was investigated using the MBEC assay, the reference procedure for biofilm susceptibility testing (. Mature *S. maltophilia* (48-hours old) were challenged for 24 hours with NAC and colistin, either alone or in combination. Viable cell count of challenged biofilms was compared to controls in order to assess the antibiofilm activity of the tested drugs and drugs/combinations.

Figure 3:
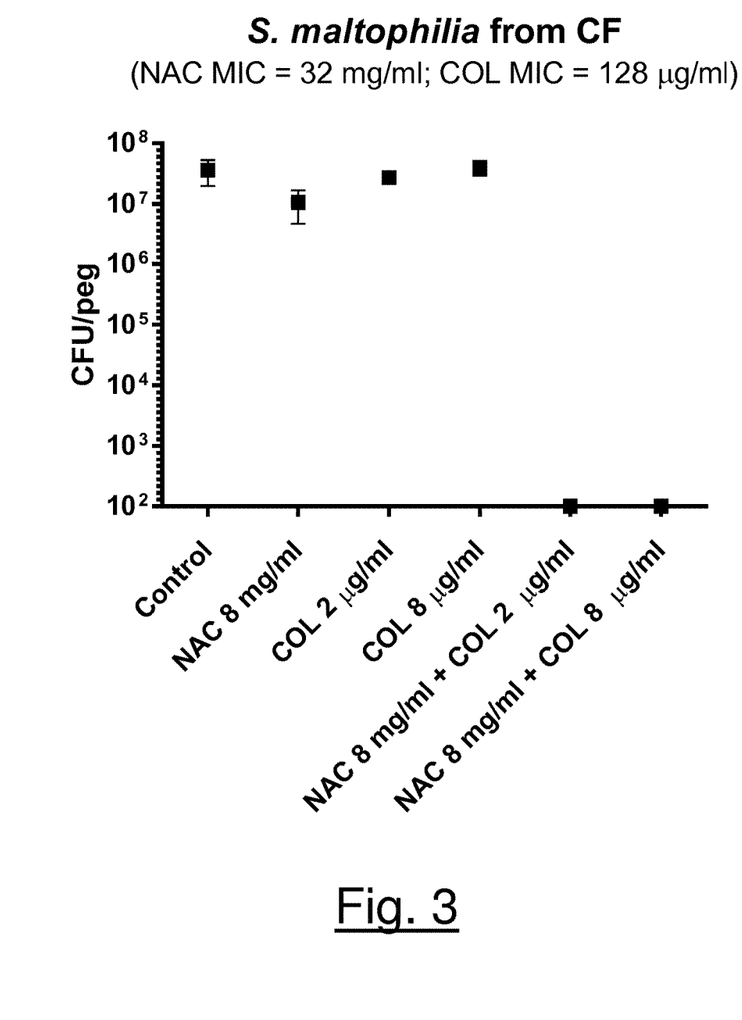
FIG. 3. Antibiofilm activity of NAC, colistin and colistin/NAC combinations (sub-MIC concentrations) tested on a Cystic Fibrosis isolate of *S. maltophilia*. Biofilms were grown on Calgary Device (MBEC assay) for 48 hrs and challenged for 24 hours with NAC alone, Colistin alone at two different concentration: 2 µg/ml and 8 µg/ml and the combination of the two (NAC 8 mg/ml+Colistin 2 µg/ml and 8 µg/ml).

Sub-MIC colistin/NAC combinations were also found to exert a relevant antibiofilm activity against mature *S. maltophilia* biofilms. In particular, NAC 8 mg/ml plus colistin 2 µg/ml accounted for a reduction of more than 3 log colony forming units (CFU)/peg compared to controls (FIG. 3).

The results show that MIC of an colistin resistant strains tested (i.e. *S. maltophilia*, n=17; *A. baumannii*, n=7) lowered at or below the susceptibility breakpoint in the presence of NAC 8 mg/ml.

The invention claimed is:
1. A method of treating a bacterial infection in patients in need thereof, said method consisting of comprising
administering to said patients a pharmaceutical effective amount of a synergistic pharmacological association consisting of N-acetylcysteine (NAC), colistin and a carrier, wherein said bacterial infection is caused by one or more pathogens selected from *S. maltophilia* and *A. baumannii* strains, wherein said synergistic pharmacological association comprises from 1.6 mg/ml to 8 mg/ml NAC in combination with from 2 µg/ml to 8 µg/ml colistin.
2. The method according to claim 1, wherein pathogens selected from *S. maltophilia* and *A. baumannii* strains express a colistin resistant phenotype.

3. The method according to claim 1, wherein the infection is a biofilm-associated infection.

4. The method according to claim 1, wherein the bacterial infection is detected in patients with a respiratory tract disease.

5. The method according to claim 4, wherein the respiratory tract disease is a chronic respiratory tract disease comprising Cystic Fibrosis (CF), bronchiectasis non-CF and chronic obstructive pulmonary disease (COPD).

6. The method according to claim 1, wherein a bacterial infection caused by *S. maltophilia* strain is detected in patients suffering from a respiratory tract disease.

7. The method according to claim 1, wherein a bacterial infection caused by *A. baumannii* strain is detected in patients suffering from a respiratory tract disease.

8. The method according to claim 4, wherein the patients are immunocompromised and/or hospitalized patients.

9. The method according to claim 1, wherein NAC and colistin are administered in either order, separately or concurrently, with overlapping or non-overlapping periods of administration.

10. The method according to claim 9, wherein NAC and colistin are administered via the same or of different administration routes.

11. The method according to claim 1, wherein NAC and colistin are concurrently administered in a single dosage form.

12. The method according to claim 1, wherein NAC and colistin are administered in separate dosage forms in either order, concomitantly or sequentially, with overlapping or non-overlapping periods of administration.

13. The method according to claim 12, wherein NAC and colistin are administered via the same or different modes of administration.

* * * * *

UNITED STATES PATENT AND TRADEMARK OFFICE
CERTIFICATE OF CORRECTION

| | |
|---|---|
| PATENT NO. | : 11,382,948 B2 |
| APPLICATION NO. | : 16/487227 |
| DATED | : July 12, 2022 |
| INVENTOR(S) | : Lucia Pallecchi, Francesco Sergio and Gian Maria Rossolini |

It is certified that error appears in the above-identified patent and that said Letters Patent is hereby corrected as shown below:

On the Title Page

Column 1, Item (73) Assignee:
--Zaambon S.P.A., Bresso (IT) should read "Zambon S.P.A., Bresso (IT)"--

Signed and Sealed this
Twenty-ninth Day of November, 2022

Katherine Kelly Vidal
*Director of the United States Patent and Trademark Office*